(12) United States Patent
Yoon

(10) Patent No.: US 12,007,169 B2
(45) Date of Patent: Jun. 11, 2024

(54) APPARATUS FOR EXTRACTING WATER FROM PLANT CONDENSER TO THE OUTSIDE FOR WATER QUALITY ANALYSIS

(71) Applicant: KEPCO ENGINEERING & CONSTRUCTION COMPANY, INC., Gimcheon-si (KR)

(72) Inventor: Chang Sun Yoon, Seoul (KR)

(73) Assignee: KEPCO ENGINEERING & CONSTRUCTION COMPANY, INC., Gimcheon-si (KR)

( * ) Notice: Subject to any disclaimer, the term of this patent is extended or adjusted under 35 U.S.C. 154(b) by 620 days.

(21) Appl. No.: 17/119,552

(22) Filed: Dec. 11, 2020

(65) Prior Publication Data
US 2021/0180868 A1 Jun. 17, 2021

(30) Foreign Application Priority Data
Dec. 16, 2019 (KR) .................. 10-2019-0168252

(51) Int. Cl.
| | |
|---|---|
| F28B 9/08 | (2006.01) |
| F28B 1/02 | (2006.01) |
| G01N 1/10 | (2006.01) |
| G01N 1/14 | (2006.01) |

(52) U.S. Cl.
CPC .............. *F28B 9/08* (2013.01); *F28B 1/02* (2013.01); *G01N 1/14* (2013.01); *G01N 2001/1031* (2013.01)

(58) Field of Classification Search
CPC ... F28B 1/02; F28B 11/00; F28B 9/08; G01N 1/14; G01N 2001/1031; G01N 2001/1037; G01N 2001/1481; G01N 33/18; G01N 1/10

USPC .................. 73/863, 83, 863.81, 863.83
See application file for complete search history.

(56) References Cited

U.S. PATENT DOCUMENTS 8,434,372 B2 5/2013 Fjerdingstad

FOREIGN PATENT DOCUMENTS

| CN | 103197038 A | * | 7/2013 |
|---|---|---|---|
| CN | 203132798 U | * | 8/2013 |
| CN | 204831837 | | 12/2015 |
| CN | 207081572 U | * | 3/2018 |
| CN | 207161075 U | * | 3/2018 |
| CN | 208043469 | | 11/2018 |

(Continued)

OTHER PUBLICATIONS

Korean Office Action for 10-2019-0168252, dated May 18, 2021.

*Primary Examiner* — Daniel S Larkin
*Assistant Examiner* — Nashmiya S Fayyaz
(74) *Attorney, Agent, or Firm* — Nixon Peabody LLP; Jeffrey L. Costellia

(57) ABSTRACT

Provided is an apparatus for extracting water from a condenser to the outside for water quality analysis. The apparatus includes an insertion pipe inserted into a condenser, a screw thrust portion including a rotating shaft inserted into the insertion pipe, a screw coupled to one end of the rotating shaft, and a screw thrust portion comprising a power providing portion configured to transmit power to the rotating shaft, and an exhaust pipe provided in the insertion pipe to introduce the water to flow to the outside of the condenser when the water contained in the condenser flows toward a rear side of the screw according to a rotation of the screw.

4 Claims, 7 Drawing Sheets

(56) References Cited

FOREIGN PATENT DOCUMENTS

| | | | |
|---|---|---|---|
| CN | 208297180 U | * | 12/2018 |
| CN | 208333963 U | * | 1/2019 |
| CN | 208333981 U | * | 1/2019 |
| JP | H-06-19344 | | 3/1994 |
| JP | H0915120 A | * | 1/1997 |
| JP | 2014-232018 | | 12/2014 |
| KR | 10-2011-0069068 | | 6/2011 |

* cited by examiner

APPARATUS FOR EXTRACTING WATER FROM PLANT CONDENSER TO THE OUTSIDE FOR WATER QUALITY ANALYSIS

CROSS-REFERENCE TO RELATED APPLICATION

This application is based on and claims priority under 35 U.S.C. § 119 to Korean Patent Application No. 10-2019-0168252, filed on Dec. 16, 2019, in the Korean Intellectual Property Office, the disclosure of which is incorporated by reference herein in its entirety.

BACKGROUND

1. Field

The disclosure relates to an apparatus for extracting water from a condenser to the outside for water quality analysis, and more particularly, to an apparatus for extracting water from a condenser to the outside for water quality analysis, in which water from a condenser is extracted to the outside by using the thrust of a screw so that equipment is miniaturized and installation and removal of the apparatus become easy.

2. Description of Related Art

A plant condenser contains feedwater. Feedwater is heated by a heater and then finally passes through a boiler and a turbine. Accordingly, it is very important to maintain the quality of feedwater at a certain level.

Referring to FIGS. 1 and 2, as a seawater pipe 2 for cooling steam is installed in a condenser 1, when seawater leaks, immediate action is necessary to detect leakage quickly and to prevent feedwater from flowing into boilers, turbines, and the like. The quality of water in the condenser 1 may be analyzed by analyzing the conductivity of water. According to the related art, the conductivity of water in the condenser 1 is analyzed by extracting feedwater from a hotwell shell 3 of the condenser 1 by using a pump 4 and transferring the extracted feedwater to water quality analysis equipment. However, as the inside of the condenser 1 is maintained in a vacuum state during a normal operation, when the pump 4 is operated after the inside of the condenser 1 was in a vacuum state, it is not easy to suck water from the condenser 1 to the outside due to insufficient pump pressure.

Furthermore, when seawater leaks, an operator locates the position of leakage by sequentially opening/closing sampling valves 5 installed at different positions in the condenser 1. The positon of leakage is located based on information such as an opening/closing state of a valve, capacity of a pump, a distance between a pump and an analyzer, and the like. However, as the storage capacity of a tray is limited to be within a few minutes, the arrival time of the feedwater to the analyzer according to the capacity of the pump 5 and the like are difficult to be accurately calculated and locating the position of leakage takes a lot of time and is difficult.

SUMMARY

Provided is an apparatus for extracting water from a condenser to the outside for water quality analysis, in which water in a condenser is extracted to the outside by using the thrust of a screw so that equipment may be miniaturized and installation and removal of the apparatus become easy.

Additional aspects will be set forth in part in the description which follows and, in part, will be apparent from the description, or may be learned by practice of the presented embodiments of the disclosure.

According to an embodiment of the disclosure, an apparatus for extracting water from a condenser to the outside for water quality analysis includes an insertion pipe inserted into a condenser, a screw thrust portion including a rotating shaft inserted into the insertion pipe, a screw coupled to one end of the rotating shaft, and a power providing portion configured to transmit power to the rotating shaft, and an exhaust pipe provided in the insertion pipe to introduce the water to flow to the outside of the condenser when the water contained in the condenser flows toward a rear side of the screw according to a rotation of the screw.

Furthermore, the apparatus may further include a water quality analyzer into which the water discharged from the exhaust pipe is introduced and which is configured to analyze quality of the water.

Furthermore, the apparatus may further include a return pipe through which the water passed through the water quality analyzer passes to return to the condenser and which is provided in the insertion pipe.

Furthermore, the apparatus may further include a guide pipe coupled to an outer wall of the condenser and guiding the insertion pipe inserted into the guide pipe; and a rotation valve detachably coupled to the guide pipe and comprising a through-hole through which the insertion pipe passes, wherein, when the insertion pipe is removed from the guide pipe, the rotation valve is rotatable to close the guide pipe.

Furthermore, the guide pipe may include a first guide pipe having one end portion coupled to the outer wall of the condenser and a second guide pipe detachably coupled to the other end portion of the first guide pipe.

Furthermore, a connection pipe portion may branch and protrude in a direction crossing a direction in which the guide pipe extends, the connection pipe being provided in the guide pipe, the rotation valve may include an insertion portion elongated in one direction to be inserted into the connection pipe portion and a grip portion provided on an upper portion of the insertion portion for a rotation of the insertion portion, and the through-hole may penetrate the insertion portion.

Furthermore, the insertion pipe may obliquely penetrate an outer wall of the condenser to be submerged in the water contained in the condenser.

Furthermore, a return pump may be provided between the water quality analyzer and the return pipe to supply the water that passed through the water quality analyzer to the return pipe.

Furthermore, the water quality analyzer may include a transmission portion configured to transmit, to the outside, data obtained from a measurement sensor configured to measure the quality of the introduced water.

Furthermore, an inlet nozzle may be coupled to a front end of the exhaust pipe and may include an entrance portion having a funnel shape that deceases in a direction in which the water is introduced and flows so that the pressure of the introduced water is increased

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1:
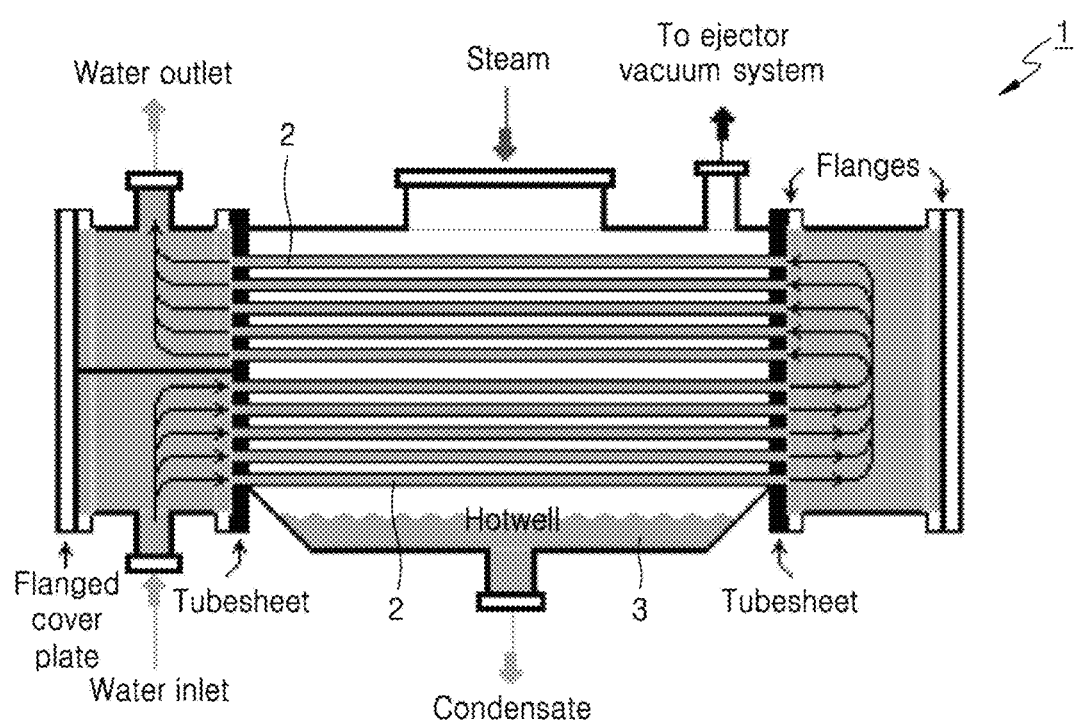
FIG. 1 is a schematic cross-sectional view of a condenser according to the related art.
Figure 2:
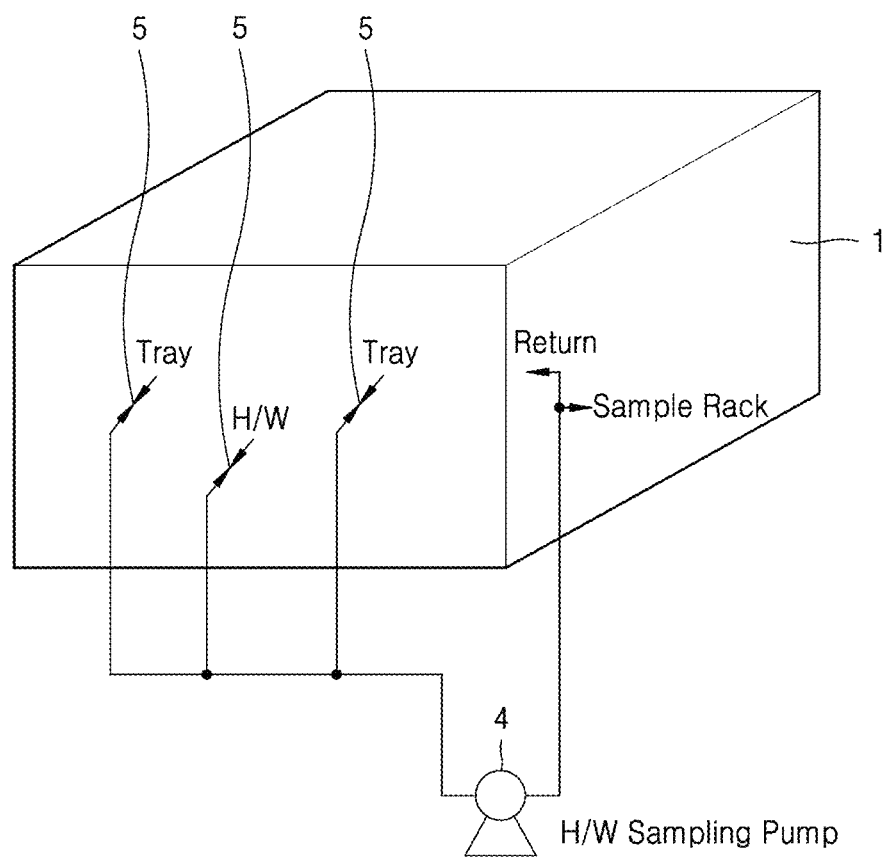
FIG. 2 is a conceptual diagram of an extraction apparatus according to the related art.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

An embodiment according to the disclosure is described below in detail with reference to the accompanying drawings.

Figure 3:
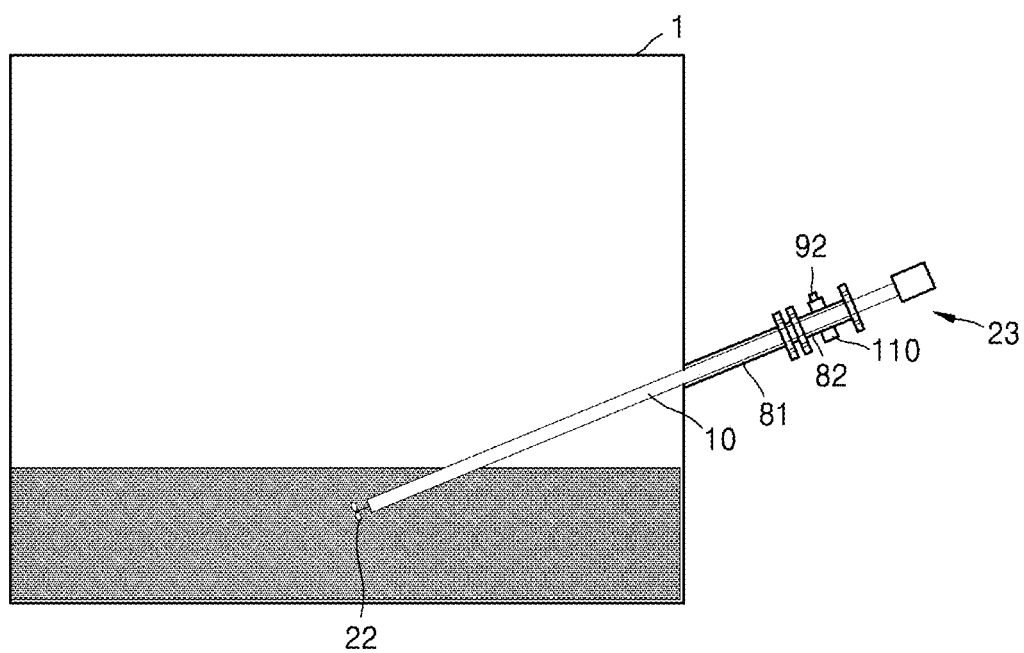
FIG. 3 is a schematic view of an extraction apparatus according to an embodiment of the disclosure, the extraction apparatus being installed in a condenser.
Figure 4:
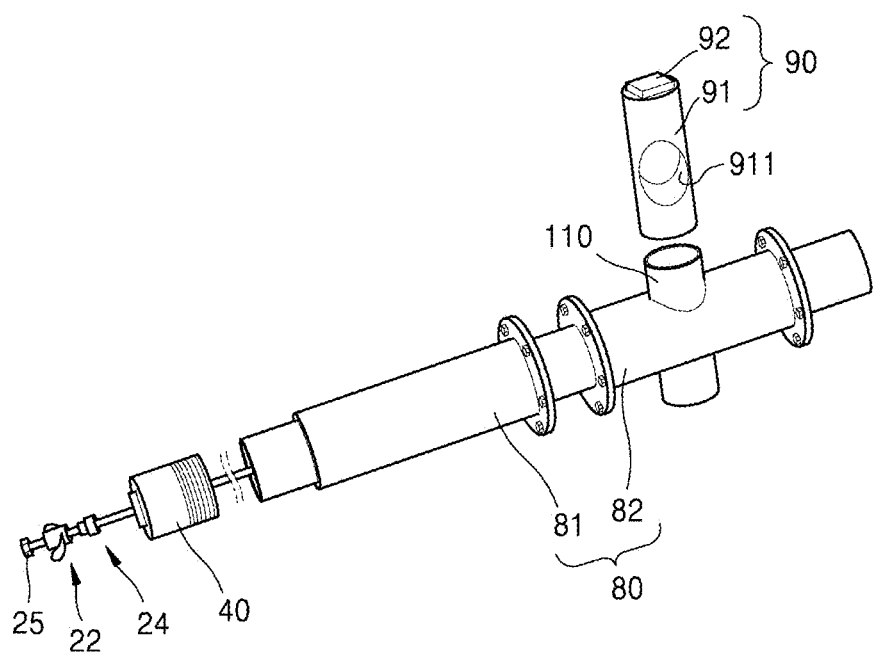
FIG. 4 is a perspective view of the extraction apparatus of FIG. 3.
Figure 5:
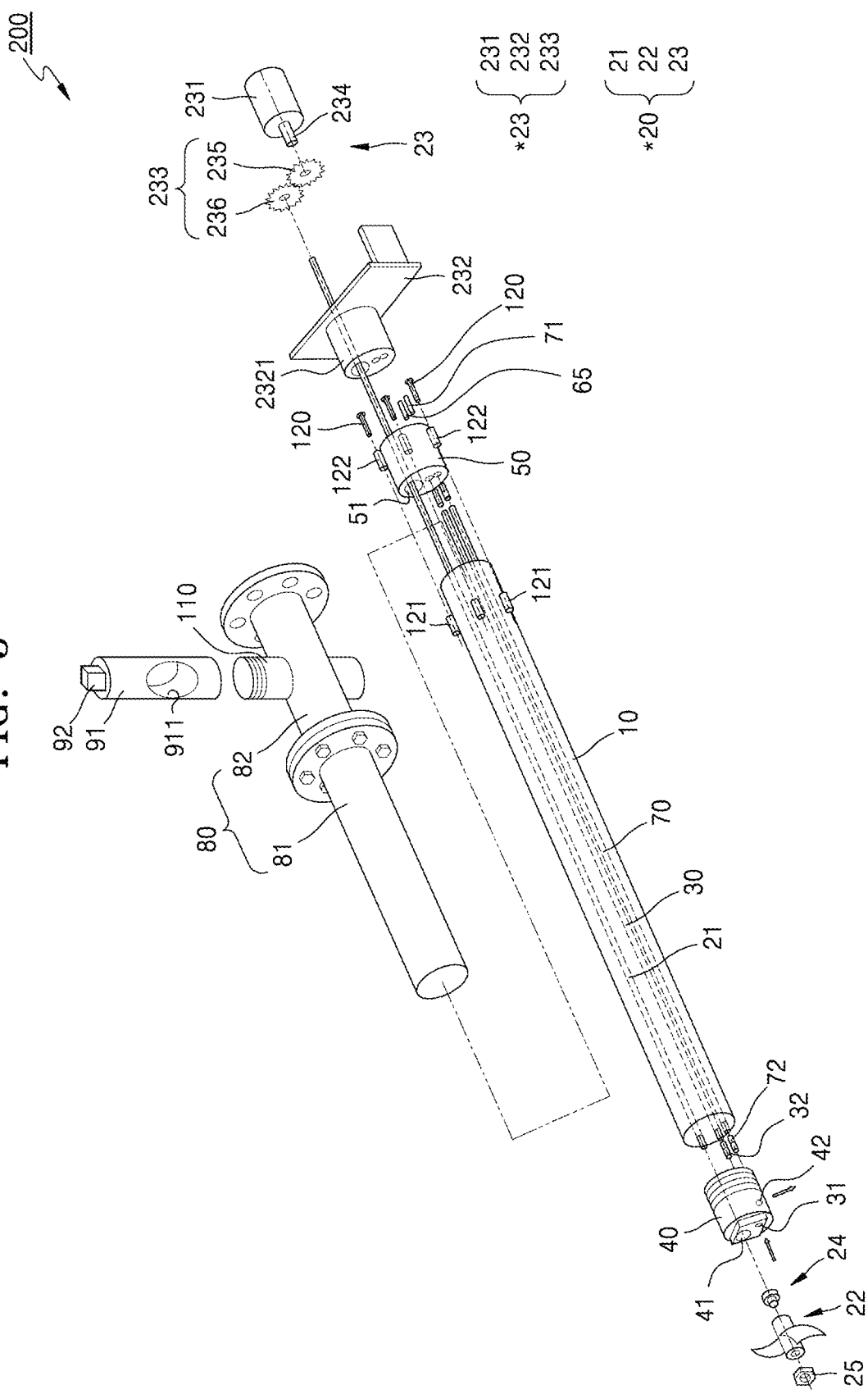
FIG. 5 is an exploded view of the extraction apparatus of FIG. 4.
Figure 6:
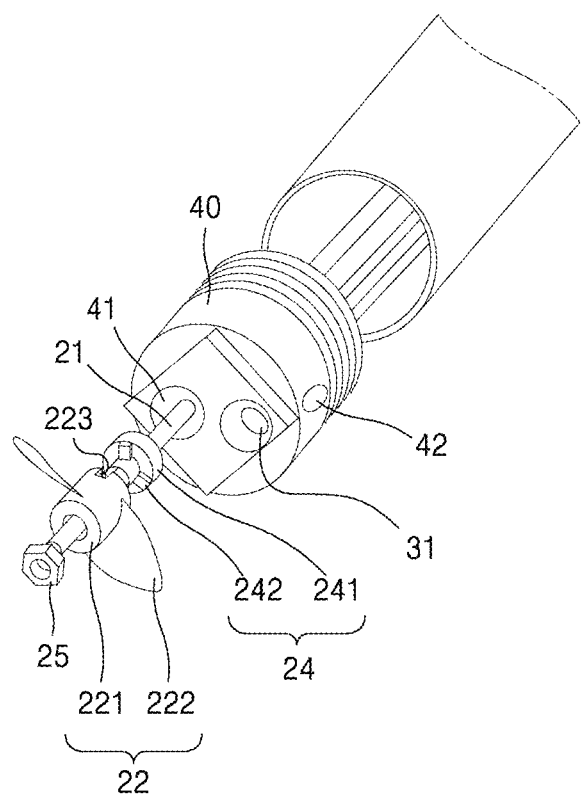
FIG. 6 illustrates a major portion of the extraction apparatus of FIG. 4.
Figure 7:
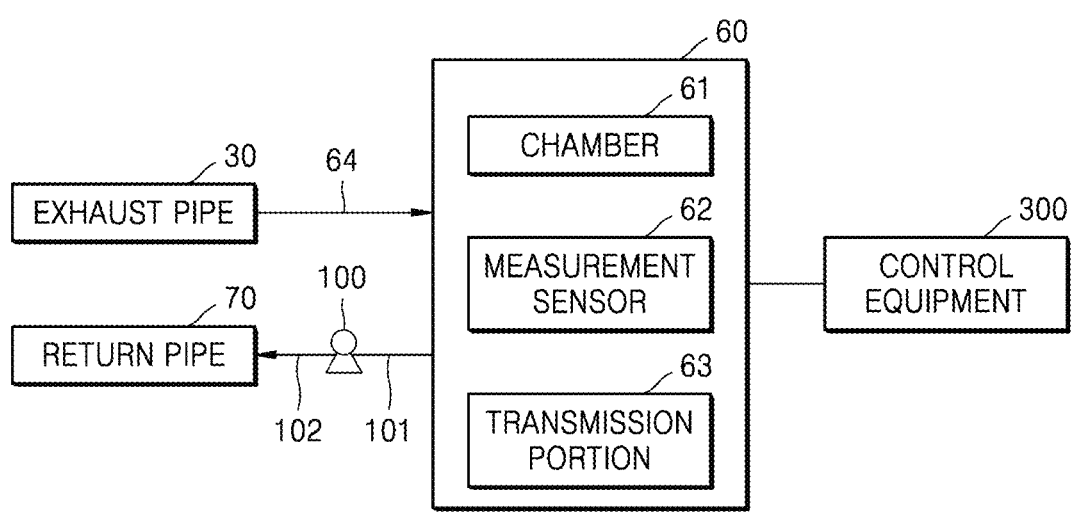
FIG. 7 is a block diagram of an extraction apparatus according to an embodiment of the disclosure.

FIG. 3 is a schematic view of an extraction apparatus according to an embodiment of the disclosure, the extraction apparatus being installed in a condenser. FIG. 4 is a perspective view of the extraction apparatus of FIG. 3. FIG. 5 is an exploded view of the extraction apparatus of FIG. 4. FIG. 6 illustrates a major portion of the extraction apparatus of FIG. 4. FIG. 7 is a block diagram of an extraction apparatus according to an embodiment of the disclosure.

Referring to FIG. 3, an apparatus 200 for extracting water from a condenser to the outside for water quality analysis according to an embodiment of the disclosure may include an insertion pipe 10, a screw thrust portion 20, and an exhaust pipe 30.

The insertion pipe 10 is a tubular member to be inserted into the condenser 1. The insertion pipe 10 obliquely penetrates an outer wall of the condenser 1. The insertion pipe 10 is installed such that an end portion of the insertion pipe 10 is submerged in water contained in the condenser 1.

The screw thrust portion 20 provides power to extract the water contained in the condenser 1 to the outside by using thrust of a screw 22. The screw thrust portion 20 may include a rotating shaft 21, the screw 22, and a power supply portion 23.

The rotating shaft 21 is inserted in the insertion pipe 10. The length of the rotating shaft 21 is formed to be longer than the length of the insertion pipe 10, and one end portion of the rotating shaft 21 protrudes from one end portion of the insertion pipe 10, and the other end portion thereof protrudes from the other end portion of the insertion pipe 10.

The screw 22 is coupled to the one end portion of the rotating shaft 21. The screw 22 may include a body portion 221 and a blade 222. A plurality of coupling recesses 223 are formed in one end portion of the body portion 221 to be separated from each other at certain intervals. An adaptor 24 that is coupled to the rotating shaft 21 is inserted into the coupling recess 223 and coupled to the coupling recess 223.

The adaptor 24 may include a fixed portion 241 fixed on the rotating shaft 21 and a protruding portion 242 protruding from the fixed portion 241 to be inserted into the coupling recess 223. A nut 25 is screw-coupled to an end portion of the rotating shaft 21 to prevent escape of the screw 22.

The power supply portion 23 is provided to supply power to the rotating shaft 21. The power supply portion 23 is provided at the other end portion of the rotating shaft 21. According to the present embodiment, the power supply portion 23 may include a motor 231, a motor fixing portion 232, and a gear portion 233.

The motor 231 generates power to rotate the rotating shaft 21. The motor 231 is fixed to the motor fixing portion 232. The gear portion 233, as a configuration to connect a motor shaft 234 of the motor 231 to the rotating shaft 21 with gears, may include a first gear 235 coupled to the motor shaft 234 and a second gear 236 coupled to the rotating shaft 21, which are engaged with each other.

According to the present embodiment, a first finish member 40 and a second finish member 50 are coupled to both end portions of the insertion pipe 10.

The first finish member 40 is coupled to one end portion of the insertion pipe 10. The screw thrust portion 20 is disposed outside the first finish member 40. A first insertion hole 41, into which the rotating shaft 21 is inserted and coupled thereto, is provided in the first finish member 40.

According to the present embodiment, the first insertion hole 41 is formed to be eccentric from the center of the first finish member 40. As the first insertion hole 41 support one end portion of the rotating shaft 21 as much as the length thereof, the rotating shaft 21 may be prevented from sagging.

The second finish member 50 is coupled to the other end portion of the insertion pipe 10. The screw thrust portion 20 is disposed outside the second finish member 50. A second insertion hole 51, into which the rotating shaft 21 is inserted, is provided in the second finish member 50.

According to the present embodiment, like the first insertion hole 41 of the first finish member 40, the second insertion hole 51 is formed to be eccentric from the center of the second finish member 50. The second insertion hole 51 supports the other end portion of the rotating shaft 21 as much as the length thereof. The second insertion hole 51 with the first insertion hole 41 may prevent the rotating shaft 21 from sagging.

The exhaust pipe 30 is provided in the insertion pipe 10 to move water in the condenser 1. The exhaust pipe 30 with the rotating shaft 21 is inserted in the insertion pipe 10. The exhaust pipe 30 introduces the water to flow to the outside of the condenser 1 when the water contained in the condenser 1 flows to the back of the screw 22 due to the rotation of the screw 22.

According to the present embodiment, an inlet nozzle 31, through which the water in the condenser 1 is introduced, is coupled to a front end of the exhaust pipe 30. The inlet nozzle 31 is inserted into the first finish member 40, and a rear end side of the inlet nozzle 31 and the front end of the exhaust pipe 30 are connected to a first connection end pipe 32 to be connected each other.

The exhaust pipe 30 may include a silicon or plastic material. The inlet nozzle 31 has an entrance portion having a funnel shape that deceases in a direction in which the water is introduced and flows so that the pressure of the introduced water is increased.

An extraction apparatus 200 according to the present embodiment may include a water quality analyzer 60, a return pipe 70, a guide pipe 80, a rotation valve 90, and a return pump 100.

The water quality analyzer 60 is provided to receive the water of the condenser 1 discharged from the exhaust pipe 30 and analyze the quality of the water. The water discharged from the exhaust pipe 30 passes through an extraction tube 64 and flows into the water quality analyzer 60. According to the present embodiment, the end portion of the exhaust pipe 30 and the extraction tube 64 are hermetically connected to each other by a second connection end pipe 65.

The water quality analyzer 60 may include a chamber 61 into which the water of the condenser 1 flows and a measurement sensor 62 provided in the chamber 61.

To quickly check the state of the quality of the water in the condenser 1, the water quality analyzer 60 may be disposed at a position relatively close to a position where the water of the condenser 1 is discharged through the exhaust pipe 30.

A specific conductivity (SC) measurement sensor may be used as the measurement sensor 62. As necessary, the SC measurement sensor and a cation conductivity (CC) measurement sensor may be simultaneously provided as the measurement sensor 62.

The water quality analyzer 60 may include a transmission portion 63 for transmitting, to the outside, data obtained from the measurement sensor 62 where the quality of the introduced water. The data is provided to a power plant control equipment 300 through a cable to be used for operating a power plant. The method of transmitting the data by the transmission portion 63 is not limited to a wired method.

The return pipe 70 is provided to return the water passed through the water quality analyzer 60 back to the condenser 1. The return pipe 70 is installed inside the insertion pipe 10. An end portion of the return pipe 70 is inserted into the first finish member 40, and an outlet hole 42 is formed in the first finish member 40 so that the water returned through the return pipe 70 flows back to the inside of the condenser 1. According to the present embodiment, a fourth connection end pipe 72 is connected to an end portion of the return pipe 70 and connected to the first finish member 50. As the water extracted from the condenser 1 by the return pipe 70 is returned back to the condenser 1, damage of water in the condenser 1 may be prevented.

The guide pipe 80 is coupled to an outer wall of the condenser 1 so that the insertion pipe 10 is inserted therein and guided thereby. The guide pipe 80 facilitates the installation and removal of the insertion pipe 10.

In detail, the guide pipe 80 may include a first guide pipe 81 having one end portion coupled to the outer wall of the condenser 1, and a second guide pipe 82 detachably coupled to the other end portion of the first guide pipe 81. The first and second guide pipes 81 and 82 may be coupled to a flange in a screw method.

For example, the first guide pipe 81 may be previously manufactured to the outer wall of the condenser 1 by a method such as welding, and the like, and the second guide pipe 82 is manufactured in different lengths suitable for environment considering the arrangement of surrounding structures and possibility of interference and detachably coupled to the first guide pipe 81.

A through-hole 911 through which the insertion pipe 10 passes is formed in the rotation valve 90, and thus the rotation value 90 is detachably coupled to the guide pipe 80. In detail, the rotation valve 90 may include an insertion portion 91 and a grip portion 92.

The insertion portion 91 is a portion that is inserted into the guide pipe 80 and coupled thereto. According to the present embodiment, a connection pipe portion 110 that is branched to protrude in a direction crossing a direction in which the guide pipe 80 extends is provided on the guide pipe 80.

According to the present embodiment, the connection pipe portion 110 is formed by extending in a direction perpendicular to the direction in which the guide pipe 80 extends. The insertion portion 91 is elongated in one direction to be inserted into the connection pipe portion 110.

The through-hole 911 is provided in the insertion portion 91. The through-hole 911 is provided to introduce the end portion of the insertion pipe 10 to be inserted into the guide pipe 80 and to be introduced into the inside of the condenser 1, while the insertion portion 91 is inserted into the guide pipe 80. In other words, the insertion pipe 10 is inserted through the through-hole 911 formed in the insertion portion 91.

The grip portion 92 is provided above the insertion portion 91 for the rotation of the insertion portion 91. According to the present embodiment, the insertion pipe 10 may be separated from the guide pipe 80. When the insertion pipe 10 is removed from the guide pipe 80, the rotation valve 90 closes the guide pipe 80 to maintain a vacuum state in the condenser 1.

As such, the grip portion 92 is provided to rotate the insertion portion 91 when the insertion pipe 10 is separated from the guide pipe 80. The grip portion 92 may have a shape corresponding to the shape of a tool suitable for rotation so that the tool may be coupled to the grip portion 92.

The return pump 100 is provided to supply the water passed through the water quality analyzer 60 to the side of the return pipe 70. The return pump 100 is provided between the water quality analyzer 60 and the return pipe 70. The return pump 100 is connected to the water quality analyzer 60 and a first return tube 101, and the return pump 100 and the return pipe 70 are connected to a second return tube 102. The second return tube 102 and the return pipe 70 are connected to each other by a third connection end pipe 71 so that easy coupling and water tightness are secured.

The operation and effect of the extraction apparatus 200 for extracting the water from the condenser 1 for analysis of the quality of the water configured as above are described below in detail.

The first guide pipe 81 is coupled to the outer wall of the condenser 1, and the second guide pipe 82 is coupled to the first guide pipe 81 by the flange. The rotation valve 90 is inserted into the connection pipe portion 110 provided in the guide pipe 80. In this state, in order for the through-hole 911 of the rotation valve 90 to open the guide pipe 80, the through-hole 911 is inserted to communicate with the guide pipe 80.

The insertion pipe 10 is inserted into the guide pipe 80 with the rotating shaft 21 and the screw 22 are provisionally assembled in the insertion pipe 10. The provisional assembly is performed according to the following process.

The rotating shaft 21 is inserted into the insertion pipe 10. The one end portion of the rotating shaft 21 is exposed through the first insertion hole 41 of the first finish member 40. The screw 22 and the adaptor 24 are coupled to the rotating shaft 21 that is exposed.

The exhaust pipe 30 and the return pipe 70 are also inserted into the insertion pipe 10 and installed therein. The exhaust pipe 30 being inserted in the insertion pipe 10 connects one end portion thereof to the inlet nozzle 31 via the first connection end pipe 32. The return pipe 70 being inserted in the insertion pipe 10 connects one end portion thereof to the first finish member 40. Next, the first finish member 40 is coupled to the end portion of the insertion pipe 10 by a screw method. In such a process, the provisional assembly of one end portion of the insertion pipe 10 is completed.

The second finish member 50 is coupled to the other end portion of the insertion pipe 10. The rotating shaft 21 is exposed through the second insertion hole 51 of the second finish member 50. The exhaust pipe 30 is inserted into the second finish member 50 and coupled thereto, and the exhaust pipe 30 is coupled to the extraction tube 64 by the second connection end pipe 65. The other end portion of the return pipe 70 is connected to the second return tube 102 by the third connection end pipe 71. The second finish member 50 is coupled to the other end portion of the insertion pipe 10 by a bolt 120. To use the bolt 120 for fastening, a first fastening portion 121 and a second fastening portion 122 are formed on the outer sides of the insertion pipe 10 and the second finish member 50. The bolt 120 is coupled to the first fastening portion 121 and the second fastening portion 122 by penetrating the same.

The insertion pipe 10 that is provisionally assembled is inserted into the guide pipe 80. The insertion pipe 10 passes through the through-hole 911 of the rotation valve 90 that is already coupled to the guide pipe 80, and the screw 22 is inserted to a position to be submerged in the water in the condenser 1.

Next, the power supply portion 23 is coupled to one end portion of the second finish member 50. The motor 231 and the gear portion 233 are coupled to the motor fixing portion 232, and a coupling portion 2321 coupled to the second finish member 50 is formed to protrude. The motor fixing portion 232 is coupled to the second finish member 50 by the coupling portion 2321.

Next, the exhaust pipe 30 is connected to the water quality analyzer 60 by the extraction tube 64. In order to introduce the water passed through the water quality analyzer 60 via the return pipe 70, the first and second return tubes 101 and 102 and the return pump 100 are connected to each other so that the installation of the extraction apparatus 200 according to the disclosure is completed.

As such, in the extraction apparatus 200 according to an embodiment of the disclosure, the screw 22 is rotated by a rotation force of the motor 231, water flowing to the rear side of the screw 22 flows to the water quality analyzer 60 via the exhaust pipe 30, and after analysis of the quality of water is performed, the water flows back to the inside of the condenser 1 via the return pipe 70, thereby forming a circulation process.

The water of the condenser 1 flows to the water quality analyzer 60 by the rotation force of the screw 22, and a pressure relationship below is established in connection with the movement of the water of the condenser 1.

According to an embodiment of the disclosure, assuming that the pressure at the rear end of the screw 22 when the screw 22 is rotated is P1, the pressure when the water of the condenser 1 is introduced into the exhaust pipe 30 is P2, the pressure needed to deliver water from the rear end of the screw 22 to the water quality analyzer 60 via the exhaust pipe 30 is P3, and the pressure lost in the exhaust pipe 30 when water is moved through the exhaust pipe 30 is P4, a condition that P1+P2>P3+P4 is satisfied. Under the above condition, the water in the condenser 1 is moved from the inside of the condenser 1 to the water quality analyzer 60 without additional configuration to absorb the water into the water quality analyzer 60.

As such, according to an embodiment of the disclosure, the extraction apparatus 200 for extracting water from a condenser to analyze the quality of the water extracts the water from the condenser 1 to the outside by using the rotation force of the screw 22 so that there is no need to consider a degree of vacuum in the condenser 1 during an operation of the condenser 1. In other words, the disclosure solves problems of the related-art method of extracting water by using a pump for analysis of the quality of water from a condenser that is kept in a vacuum state during an operation of a power plant, which causes an overload to the pump so that the pump may be damages, and in which lot of cost is incurred in the replacement and maintenance of a pump.

Furthermore, the extraction apparatus 200 according to the disclosure provides an effect of saving costs by omitting piping construction for connecting a pump to multiple positions in a lower portion of a condenser according to the related art.

Furthermore, as the length of the insertion pipe 10 installed in the condenser 1 is manufactured in various way and thus the insertion pipe 10 may be installed at a desired position of the condenser 1, the installation and removal thereof is easy, and equipment may be simplified by reducing the length of the insertion pipe 10.

Furthermore, when the extraction apparatus 200 according to the disclosure is installed at multiple positions in the condenser 1, the quality of water may be analyzed at each position where the extraction apparatus 200 is installed, so that a seawater leak point may be quickly and easily located. In other words, according to the related art, when a plurality of pipes are connected to a pump for analyzing the quality of water, a leak point is located by checking valves connected to the respective pipes by sequentially closing the valves to check a damaged pipe. However, the disclosure provide an effect of quickly and conveniently checking a leak point.

Furthermore, as the insertion pipe 10 employed in the disclosure may be separated from the guide pipe 80, maintenance or repair is convenient, and as the guide pipe 80 may be closed by rotating the rotation valve 90 when the insertion pipe 10 is separated from the guide pipe 80, loss of vacuum of the condenser 1 may be prevented in advance.

The disclosure may be used to extract a liquid in various containers used in a power plant, and also may be applied in replacement of various underwater pumps used at industrial sites.

As the apparatus for extracting water from a condenser to the outside for water quality analysis according to the disclosure extracts water from a condenser to the outside by using the rotation force of a screw, there is no need to consider a degree of vacuum in the condenser during an operation of the condenser, and there is no possibility of damage of a motor for transmitting a rotation force to the screw by the vacuum in the condenser.

Furthermore, as an insertion pipe to be installed on the condenser is manufactured with various lengths and installed at a desired portion of the condenser, the installation and removal thereof is easy, and equipment may be simplified by reducing the length of the insertion pipe.

Furthermore, when the extraction apparatus according to the disclosure is installed at multiple positions in the condenser, the quality of water may be analyzed at each individual position where the extraction apparatus is installed, and thus a seawater leak point may be quickly and easily located.

Furthermore, as the insertion pipe employed in the disclosure may be separated from the guide pipe, maintenance or repair is convenient, and furthermore when the insertion pipe is separated from the guide pipe, a rotation valve provided in the guide pipe closes the guide pipe, a vacuum state of the condenser may be maintained.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope of the disclosure as defined by the following claims.

What is claimed is:

1. An apparatus for extracting water from a condenser to the outside for water quality analysis, the apparatus comprising:
    an insertion pipe inserted into a condenser;
    a screw thrust portion comprising a rotating shaft inserted into the insertion pipe, a screw coupled to one end of the rotating shaft, and a power providing portion configured to transmit power to the rotating shaft;
    an exhaust pipe provided in the insertion pipe to introduce the water to flow to outside of the condenser when the water contained in the condenser flows toward a rear side of the screw according to a rotation of the screw;
    a guide pipe coupled to an outer wall of the condenser and guiding the insertion pipe inserted into the guide pipe; and
    a rotation valve detachably coupled to the guide pipe and comprising a through-hole through which the insertion pipe passes,
    wherein, when the insertion pipe is removed from the guide pipe, the rotation valve is rotatable to close the guide pipe.

2. The apparatus of claim 1, wherein the guide pipe comprises a first guide pipe having one end portion coupled to the outer wall of the condenser and a second guide pipe detachably coupled to another end portion of the first guide pipe.

3. The apparatus of claim 1, wherein
    a connection pipe portion branches and protrudes in a direction crossing a direction in which the guide pipe extends, the connection pipe being provided in the guide pipe,
    the rotation valve comprising an insertion portion elongated in one direction to be inserted into the connection pipe portion and a grip portion provided on an upper portion of the insertion portion for a rotation of the insertion portion, and
    the through-hole penetrates the insertion portion.

4. The apparatus of claim 1, wherein the insertion pipe obliquely penetrates an outer wall of the condenser to be submerged in the water contained in the condenser.

* * * * *